(12) United States Patent
Lee et al.

(10) Patent No.: US 12,025,578 B2
(45) Date of Patent: Jul. 2, 2024

(54) WELDING FAILURE INSPECTION METHOD

(71) Applicant: LG ENERGY SOLUTION, LTD., Seoul (KR)

(72) Inventors: Jung Hoon Lee, Daejeon (KR); Su Taek Jung, Daejeon (KR); Seok Jin Kim, Daejeon (KR); Ji Hoon Lee, Daejeon (KR); Sang Hyun Koo, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 221 days.

(21) Appl. No.: 17/771,163

(22) PCT Filed: Dec. 29, 2020

(86) PCT No.: PCT/KR2020/019247
§ 371 (c)(1),
(2) Date: Apr. 22, 2022

(87) PCT Pub. No.: WO2021/172728
PCT Pub. Date: Sep. 2, 2021

(65) Prior Publication Data
US 2022/0412911 A1 Dec. 29, 2022

(30) Foreign Application Priority Data
Feb. 26, 2020 (KR) .................. 10-2020-0023657

(51) Int. Cl.
*G01R 27/08* (2006.01)
*B23K 26/21* (2014.01)
(Continued)

(52) U.S. Cl.
CPC ............. *G01N 27/20* (2013.01); *B23K 26/21* (2015.10); *B23K 31/125* (2013.01); *H01M 10/48* (2013.01); *H01M 50/536* (2021.01)

(58) Field of Classification Search
CPC .... G01N 27/20; G01N 33/207; B23K 31/125; B23K 26/21; B23K 2101/38;
(Continued)

(56) References Cited

U.S. PATENT DOCUMENTS

| 7,988,745 B2 | 8/2011 | Okabe et al. |
| 2001/0045414 A1 | 11/2001 | Lyshkow |

(Continued)

FOREIGN PATENT DOCUMENTS

| CN | 103376278 | * 10/2013 |
| CN | 103376278 B | 10/2013 |

(Continued)

OTHER PUBLICATIONS

Extended European Search Report issued in corresponding European Patent Application No. 20921672.0 dated Nov. 7, 2022.
(Continued)

*Primary Examiner* — Thang X Le
(74) *Attorney, Agent, or Firm* — Morgan, Lewis & Bockius LLP (57) ABSTRACT

A method for inspecting a welding defect of the present invention includes: a threshold resistance setting step (S100) of measuring a resistance of a welded portion of a sample group and deriving a threshold resistance value which becomes an evaluation standard of a weak welding; a resistance measuring step (S200) of measuring a resistance value of a welded portion to be inspected; and a step (S300) of determining as a weak welding if the resistance value measured in the resistance measuring step exceeds the threshold resistance value, wherein the threshold resistance setting step (S100) and the resistance measuring step (S200) include measuring a resistance using a microresistance measuring instrument having a resolution of nanoohm to microohm units.

(Continued)

The welding defect inspection method of the present invention shows excellent detection power for the welding defect by a weak welding.

13 Claims, 6 Drawing Sheets

(51) Int. Cl.
*B23K 31/12* (2006.01)
*G01N 27/20* (2006.01)
*H01M 10/48* (2006.01)
*H01M 50/536* (2021.01)

(58) Field of Classification Search
CPC .. H01M 10/48; H01M 50/531; H01M 50/536; Y02P 70/50; Y02E 60/10
See application file for complete search history.

(56) References Cited

U.S. PATENT DOCUMENTS

| | | |
|---|---|---|
| 2009/0233174 A1 | 9/2009 | Okabe et al. |
| 2010/0232678 A1* | 9/2010 | Hasegawa ............... B21C 37/08 |
| | | 382/141 |
| 2011/0221448 A1* | 9/2011 | Sowders ............... H01H 83/12 |
| | | 324/510 |
| 2013/0186868 A1* | 7/2013 | Das ...................... B23K 11/241 |
| | | 219/91.1 |
| 2017/0322168 A1* | 11/2017 | Lupienski ............. H01M 10/04 |
| 2021/0132154 A1* | 5/2021 | Kasper ................... G01N 27/20 |

FOREIGN PATENT DOCUMENTS

| | | |
|---|---|---|
| CN | 107607592 A | 1/2018 |
| CN | 108181356 A | 6/2018 |
| JP | 2000-100465 A | 4/2000 |
| JP | 2000-268887 A | 9/2000 |
| JP | 2003-014676 A | 1/2003 |
| JP | 4330690 B2 | 9/2009 |
| JP | 2012-200765 A | 10/2012 |
| JP | 5082861 B2 | 11/2012 |
| KR | 10-0886572 B1 | 3/2009 |
| KR | 10-2013-0097990 A | 9/2013 |
| KR | 10-2014-0141289 A | 12/2014 |
| KR | 10-2017-0125707 A | 11/2017 |
| KR | 10-1887148 B1 | 8/2018 |
| KR | 10-2057781 B1 | 12/2019 |

OTHER PUBLICATIONS

International Search Report (with partial translation) and Written Opinion dated Apr. 5, 2021 issued in corresponding International Patent Application No. PCT/KR2020/019247.

* cited by examiner

WELDING FAILURE INSPECTION METHOD

TECHNICAL FIELD

This application claims the benefit of priority based on Korean Patent Application No. 10-2020-0023657, filed on Feb. 26, 2020, and the entire contents of the Korean patent application are incorporated herein by reference.

The present invention relates to a method for inspecting a welding defect, and more particularly, to a method for inspecting whether there is a welding defect by a weak welding on the welded portion between an electrode tab and an electrode tab or between an electrode tab and an electrode lead in a lithium secondary battery.

BACKGROUND ART

In general, a secondary battery, unlike a primary battery that cannot be charged, means a battery that can be charged and discharged, and is widely used in electronic devices such as mobile phones, notebook computers, camcorders, or electric vehicles. In particular, the lithium secondary battery has a larger capacity than a nickel-cadmium battery or a nickel-hydrogen battery, and because the energy density per unit weight is high, the degree of utilization thereof is rapidly increasing.

Further, lithium secondary batteries are classified according to the structure of the electrode assembly having a positive electrode/separator/negative electrode structure. Representative examples thereof include a jelly-roll electrode assembly in which long sheet type positive electrodes and negative electrodes are wound with a separator interposed therebetween, a stacked electrode assembly in which a plurality of positive and negative electrodes cut in a predetermined size unit are sequentially stacked with a separator interposed therebetween, and a stacked/foldable electrode assembly in which bi-cells or full cells, in which positive and negative electrodes of a predetermined unit are stacked with a separator interposed therebetween, are wound.

In recent years, a pouch type battery having a stack type or stack/folding type electrode assembly embedded in a pouch-shaped battery case of an aluminum laminate sheet has attracted a lot of attention due to its low manufacturing cost and small weight, and the amount used thereof is gradually increasing.

The lithium secondary battery mainly uses a lithium-based oxide and a carbon material as a positive electrode active material and a negative electrode active material, respectively. The lithium secondary battery includes an electrode assembly, in which a positive electrode plate and a negative electrode plate coated with the positive electrode active material and the negative electrode active material, respectively, are disposed with a separator interposed therebetween, and an exterior material that seals and stores the electrode assembly together with the electrolyte.

At this time, a plurality of positive electrode tabs, which are extended from a plurality of positive electrode plates, and a plurality of negative electrode tabs, which are extended from a plurality of negative electrode plates, are formed in the electrode assembly, and the plurality of positive electrode tabs and the plurality of negative electrode tabs are respectively coupled with the positive electrode lead and the negative electrode lead by welding. Herein, a plurality of positive electrode tabs and a plurality of negative electrode tabs form an electrode tab, and a positive electrode lead and a negative electrode lead form an electrode lead.

Likewise, when the electrode tab and the electrode lead are welded, if a weak welding is performed between the electrode tabs and between the electrode tab and the electrode lead, a welding defect may be generated. Hence, there is a need for a process of inspecting whether there is a welding defect by such a weak welding.

Conventionally, in order to inspect a welding defect by a weak welding on the welded portion, tensile strength was measured by pulling the welded portion in an opposite direction. However, when using such a method, the electrode tab or the electrode lead may be damaged in the process of measuring the tensile strength. Hence, complete enumeration was not possible.

Korean Patent 2017-0125707 discloses a technology of dividing a welded portion, which is generated by coupling electrode foil elements and terminals, into a plurality of sections, measuring the resistance for each section by applying electric current to each section, and then determining that there is a welding defect if the measured resistance is greater than a threshold resistance. However, in the above literature, the correlation between the tensile strength and the resistance in the welded portion is used in deriving the threshold resistance, and thus in order to derive the threshold resistance, a process of measuring the tensile strength of the welded portion is essential.

However, conventionally, the tensile strength of the welded portion is measured by pulling the welded portion in an opposite direction, which may cause an error. Hence, the reliability of the threshold resistance value derived from the correlation between the tensile strength and the resistance is not high.

Therefore, there is a need for a technology about a method for inspecting a weak welding of a welded portion with excellent detection power while allowing complete enumeration.

DISCLOSURE

Technical Problem

As such, the present invention was devised to solve the above problems, and an object of the present invention is to provide a method for inspecting a weak welding of a welded portion with excellent detection power while allowing complete enumeration.

Technical Solution

A method for inspecting a welding defect for achieving the above purposes of the present invention includes: a threshold resistance setting step (S100) of measuring a resistance of a welded portion of a sample group and deriving a threshold resistance value which becomes an evaluation standard of a weak welding; a resistance measuring step (S200) of measuring a resistance value of a welded portion to be inspected; and a determination step (S300) of determining the welded portion as a weak welding if the resistance value measured in the resistance measuring step exceeds the threshold resistance value, wherein the threshold resistance setting step (S100) and the resistance measuring step (S200) include measuring a resistance using a microresistance measuring instrument having a resolution of nanoohm to microohm units.

In one specific example, the resistance measuring step (S200) includes measuring a resistance by allowing two resistance measuring probes to contact the welded portion.

In one specific example, the method may further include measuring a total resistance of the welded portion by allowing one resistance measuring probe to contact one end of the welded portion and allowing another resistance measuring probe to contact an other end of the welded portion.

In one specific example, the resistance measuring probe includes a voltage probe and a current probe.

In one specific example, the resistance measuring step (S200) includes measuring a resistance of a welded portion by a 4-wire type measuring scheme.

In one specific example, the resistance measuring step (S200) includes measuring a resistance of a welded portion by a direct current scheme.

In one specific example, the threshold resistance setting step (S100) includes: a data construction step (S110) of measuring a microresistance of nanoohm and microohm units for a sample group and storing the measured microresistance; and a threshold resistance value deriving step (S120) of deriving a threshold value by processing data accumulated by the data construction step (S110) by a statistical scheme.

In one specific example, a number of objects of the sample group is equal to or greater than 100,000.

In one specific example, resistance values of the sample group form a normal distribution curve.

In one specific example, the threshold resistance value is an average value+6σ.

In one specific example, the welded portion is formed by a ultrasonic welding. At this time, the resistance is measured by allowing the resistance measuring probe to contact an interface of the welded portion.

In one specific example, the welded portion is formed by a laser welding. At this time, the resistance is measured by allowing the resistance measuring probe to contact an outer peripheral surface of the welded portion.

The method for inspecting a welding defect of the present invention is preferably applied to a welded portion between an electrode lead and an electrode tab of a pouch-type secondary battery, or a welded portion between an electrode tab and an electrode tab.

Advantageous Effects

According to the welding defect inspection method of the present invention, resistances of a sample group are measured, a threshold resistance value is set from a normal distribution curve of the measured resistance values, and resistances are precisely measured by using a microresistance measuring instrument having a resolution of nanoohm to microohm levels when measuring resistances for the sample group and the welded portion to be inspected, thereby showing an excellent detection power for a weak welding defect.

DETAILED DESCRIPTION OF THE PREFERRED EMBODIMENTS

Hereinafter, preferred embodiments of the present invention will be described in detail with reference to the accompanying drawings. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

Accordingly, the embodiments described in the specification and the configurations described in the drawings are only the most preferred embodiments of the present invention, and do not represent all of the technical ideas of the present invention. It is to be understood that there may be various equivalents and variations in place of them at the time of filing the present application.

Also, throughout the specification, when an element is referred to as "including" an element, it is understood that the element may include other elements as well unless specifically stated otherwise.

Figure 1:
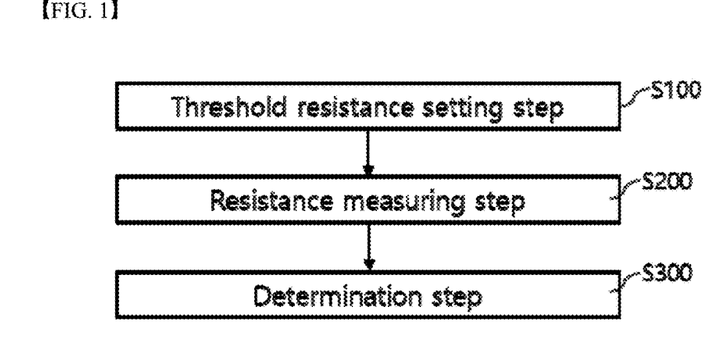
FIG. 1 is a flowchart illustrating a method of inspecting a welding defect of the present invention.

FIG. 1 is a flowchart of a method for inspecting a welding defect according to the present invention. Referring to FIG. 1, a method for inspecting a welding defect of the present invention includes: a threshold resistance setting step (S100) of measuring a resistance of a welded portion of a sample group and deriving a threshold resistance value which becomes an evaluation standard of a weak welding; a resistance measuring step (S200) of measuring a resistance value of a welded portion to be inspected; and a determination step (S300) of determining the welded portion as a weak welding if the resistance value measured in the resistance measuring step exceeds the threshold resistance value, wherein the threshold resistance setting step (S100) and the resistance measuring step (S200) include measuring a resistance using a microresistance measuring instrument having a resolution of nanoohm to microohm units.

Figure 2:
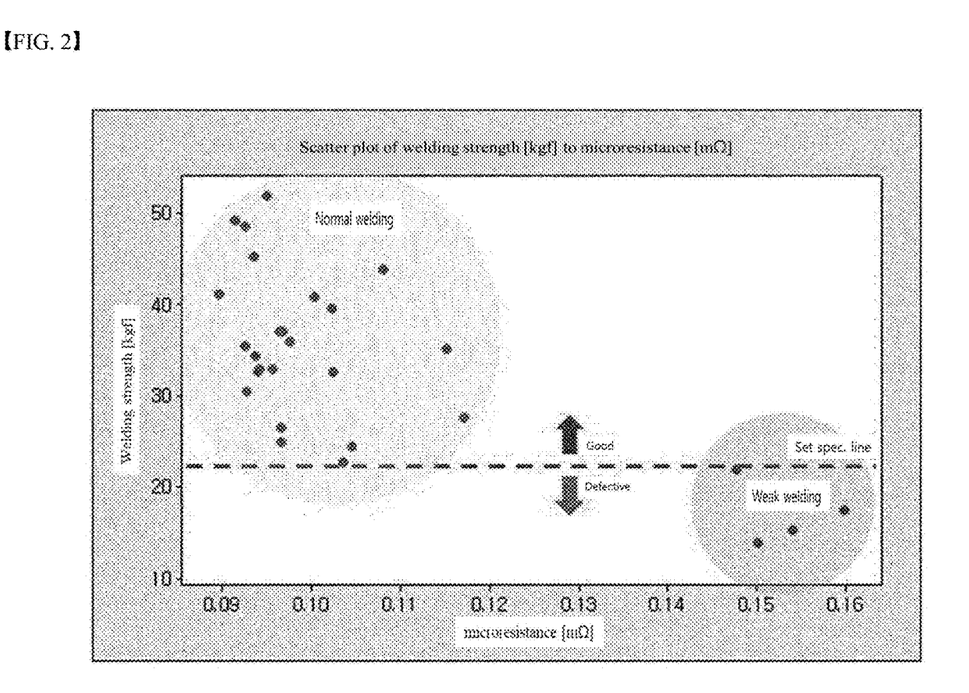
FIG. 2 is a graph showing the correlation between welding strength and resistance.

The inventors of the present invention have found that the electric resistance value of the welded portion having a low welding strength was greater than the electric resistance value of the welded portion having a normal welding strength, which has led them to the present invention. Referring to FIG. 2, a resistance value of a welded portion having been welded by a normal welding strength of 22 kgf or more is smaller than a resistance value of a welded portion having been welded by a weak welding strength less than 22 kgf. Conventionally, there was a technology of inspecting a welding defect by measuring the resistance of the welded portion and comparing the measured resistance value with the threshold resistance value. However, in the conventional technology, the method of deriving the threshold resistance value was not specific, or a process of measuring the tensile strength of the welded portion was necessary because the correlation between the tensile strength of the welded portion and the resistance was used when deriving the threshold resistance value.

However, the present invention is characterized in introducing a statistical scheme in deriving a threshold resistance value while not relying on a correlation between a tensile strength and a resistance of a welded portion and in precisely measuring a resistance by measuring the resistance up to nanoohm to microohm levels by increasing the resolution.

Namely, when the resistances for objects forming a large amount of sample groups are measured, the measured resistance values form a normal distribution curve. In the normal distribution curve, an object having a large deviation may be easily assumed as being defective from a standpoint of a statistical probability, and thus a predetermined deviation is determined as a threshold resistance value. Further, this approach is based on a premise that data for the sample group are reliable. Hence, a microresistance measuring instrument capable of precisely measuring the resistance up to nanoohm to microohm levels for the sample group is used in the process of setting a threshold value, and a microresistance measuring instrument capable of precisely measuring the resistance up to nanoohm to microohm levels is used when measuring the resistance for the object to be inspected. Likewise, in the present invention, a threshold resistance value is statistically derived from a large amount of sample groups when deriving the threshold resistance value. Hence, it is not necessary to separately measure the tensile strength of the welded portion in order to set the threshold resistance value unlike the conventional technology.

First, the threshold resistance setting step (S100) will be described.

The threshold resistance setting step (S100) according to an embodiment of the present invention includes: a data construction step (S110) of measuring a microresistance of nanoohm and microohm units for a sample group and storing the measured microresistance; and a threshold resistance value deriving step (S120) of deriving a threshold value by processing data accumulated by the data construction step (S110) by a statistical scheme.

The data construction step (S110) includes a process of measuring the resistance of a welded portion for objects which form a sample group. At this time, the number of objects of the sample group is at least 100,000, preferably 200,000, and it is preferable to have as many objects of the sample group as possible in terms of reliability.

In the data construction step (S110), resistances for objects of the sample group are measured by using a microresistance measuring instrument having a resolution of nanoohm (nΩ) to microohm (uΩ) units. This is to accumulate more reliable data. Further, the microresistance measuring method is performed in the same manner as that of the scheme of measuring the resistance of the welded portion in the resistance measuring step (S200). The threshold resistance value deriving step (S120) includes deriving a threshold resistance value by processing data accumulated by the data construction step (S110) by a statistical scheme. The statistical processing method according to an embodiment of the present invention is to obtain a normal distribution curve of the resistance value of an object of the sample group and to the +6σ value in the normal distribution curve as the threshold resistance value.

Figure 3:
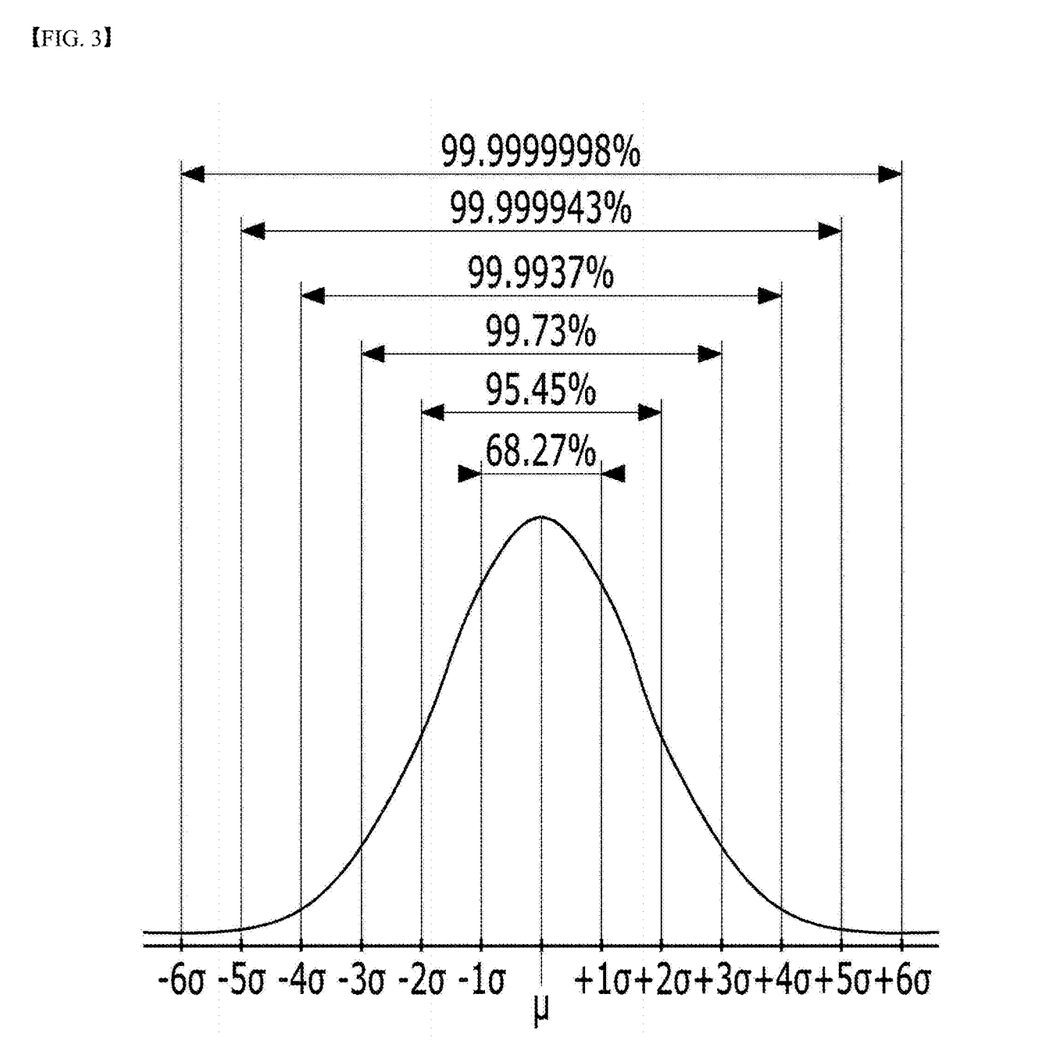
FIG. 3 is a normal distribution curve of resistance values of a sample group according to an embodiment of the present invention.

FIG. 3 shows an example of a distribution curve of resistances of a sample group according to an embodiment of the present invention. Referring to FIG. 3, when the sample group shows a normal distribution curve as in FIG. 3, the majority of objects have values close to the average value (μ), and the number of objects having a value, which is significantly deviated from the average value (μ), is small. Therefore, objects having a value, which is significantly deviated from the average value, may be stochastically assumed as being defective. Specifically, the probability that an object having a deviation of 1σ (standard deviation) appears is about 32%, the probability that an object having a deviation of 2σ appears is about 5%, the probability that an object having a deviation of 3σ appears is about 0.3%, the probability that an object having a deviation of 4σ appears is about 0.01%, the probability that an object having a deviation of 5σ appears is about 0.001%, and the probability that an object having a deviation of 6σ appears is about 0.0000001%.

As such, in an embodiment of the present invention, the sum of the average value and 6σ was set as the threshold resistance value.

Hereinafter, the resistance measuring step (S200) will be described in detail.

Figure 4:
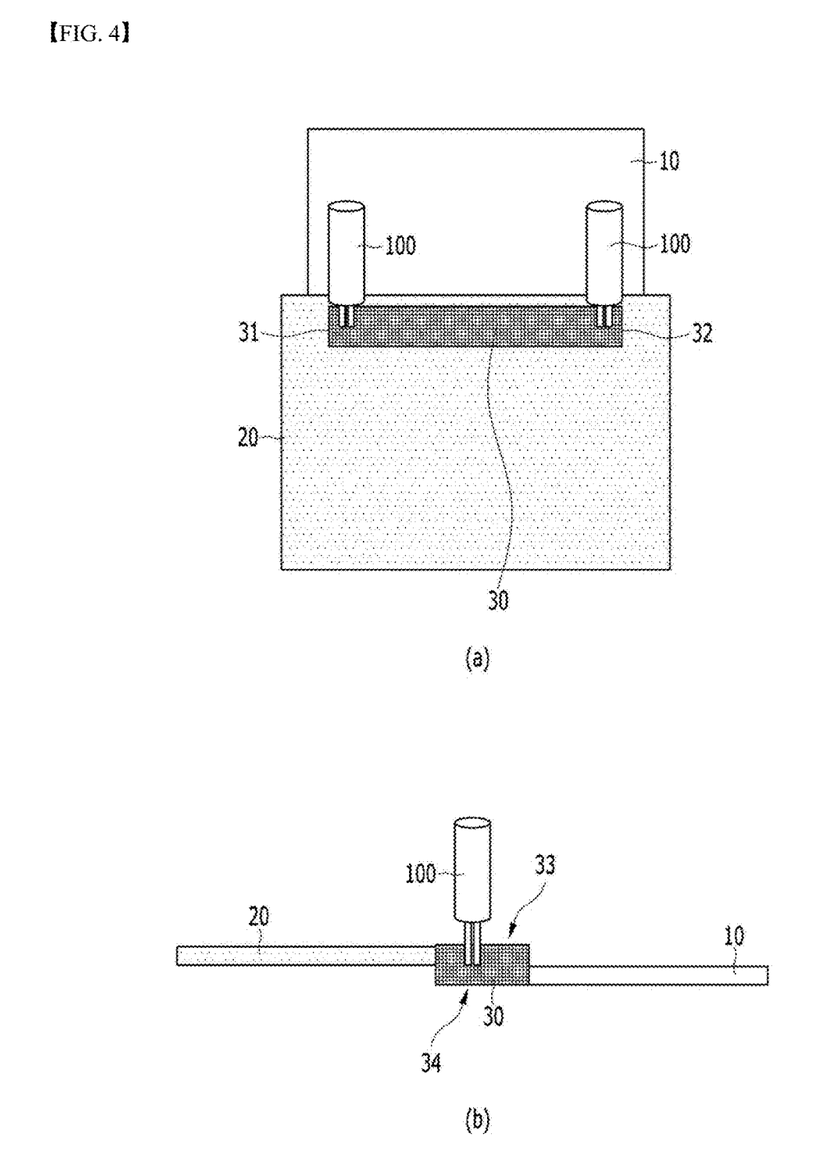
FIG. 4 is a schematic diagram showing a method of measuring a resistance according to an embodiment of the present invention.

FIG. 4 is a schematic diagram showing a method of measuring a resistance according to an embodiment of the present invention. Referring to FIG. 4, a microresistance measuring instrument, which is used for resistance measurement in the resistance measuring step (S200) of the present invention, includes two resistance measuring probes 100, and resistances are measured by allowing the two resistance measuring probes to contact the welded portion 30.

The resistance of the entire welded portion 30 can be measured by allowing one resistance measuring probe to contact one end 31 of the welded portion and allowing the other resistance measuring probe to contact the other end of the welded portion.

Figure 5:
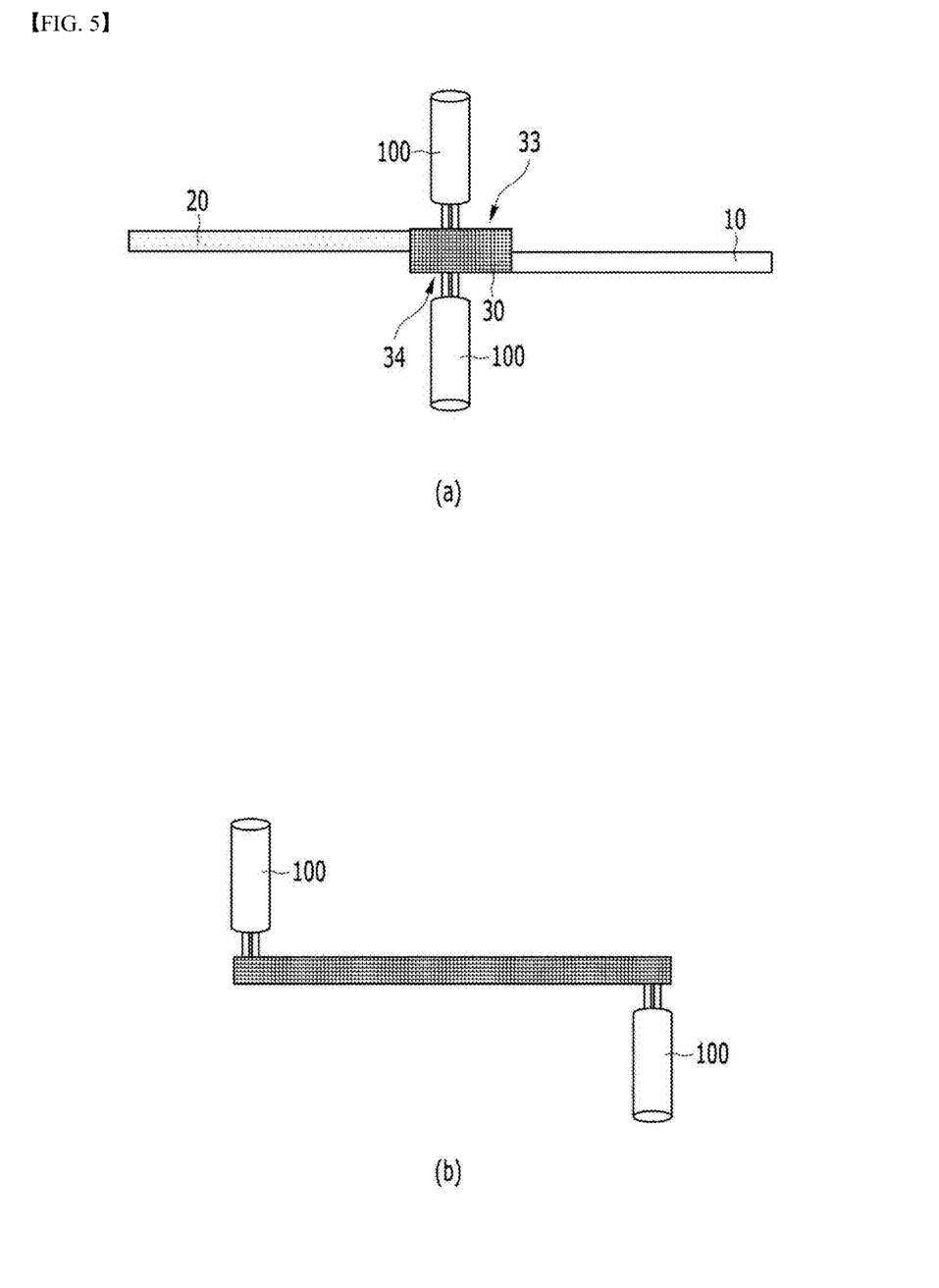
FIG. 5 is a schematic diagram showing a method of measuring a resistance according to another embodiment of the present invention.

Further, as illustrated in FIG. 4(b), the welded portion 30 can be divided into a welded portion 33 of the electrode tab 20 portion and a welded portion 34 of the electrode lead 10, and as illustrated in FIG. 4(b), both of the two resistance measuring probes can be allowed to contact the welded portion 33 of the electrode tab 20. Unlike this, both of the two resistance measuring probes may be allowed to contact the welded portion 34 of the electrode lead 10. Alternatively, as illustrated in FIG. 5, one resistance measuring probe may be allowed to contact the welded portion 33 of the electrode tab 20, and the remaining one resistance measuring probe may be allowed to contact the welded portion 34 of the electrode lead 10, to thereby measure the resistance. Among the above embodiments, it was most preferable to measure the resistance in the form of contacting both of the two resistance measuring probes on the welded portion 33 of the electrode tab 10 in terms of the detection power of detecting a weak welding.

Figure 6:
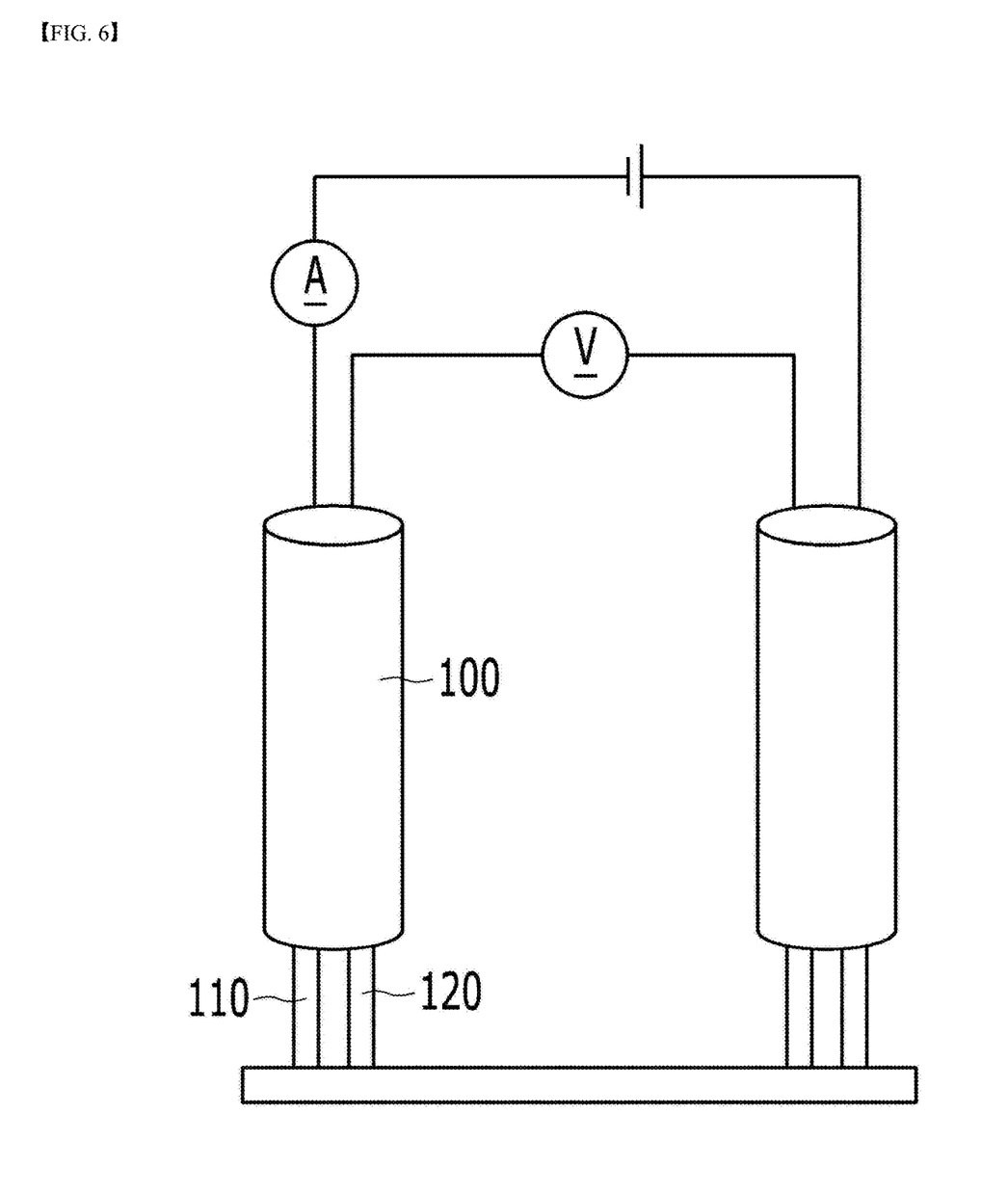
FIG. 6 is a schematic diagram of a resistance measuring probe of the present invention.

FIG. 6 shows a schematic diagram of a resistance measuring probe of the present invention, and referring to FIG. 6, the resistance measuring probe 100 of the present invention includes a current probe 110 and a voltage probe 120. The current probe applies current to a welded portion to be measured, and the voltage probe measures voltages. As such, the resistance of the welded portion can be measured.

In the present invention, the resistance is measured by allowing two resistance measuring probes to contact the welded portion. As such, the resistance of the welded portion can be measured by a 4-wire type measuring scheme. Since the 4-wire type resistance measuring scheme is less influenced by the contact resistance compared to the 2-wire type resistance measuring scheme, the microresistance can be more precisely measured in the 4-wire type resistance measuring scheme, in which the resistance can be measured even in nanoohm units.

In one specific example, the resistance measuring step (S200) includes measuring a resistance of a welded portion by a direct current scheme. The direct current scheme has an advantage that high-precision resistance measurement is possible, compared to the alternating current scheme.

The welding defect inspection method of the present invention can be widely applied to the welded portion of the secondary battery and can be applied to the welded portion according to various welding schemes. Namely, the welding defect inspection method of the present invention can be applied to a welded portion between an electrode tab and an electrode tab, a welded portion between an electrode tab and an electrode lead, and a welded portion between an electrode lead and a bus bar in a battery pack, and may also be applied to a welded portion by ultrasonic welding and a welded portion by laser welding, etc.

Figure 7:
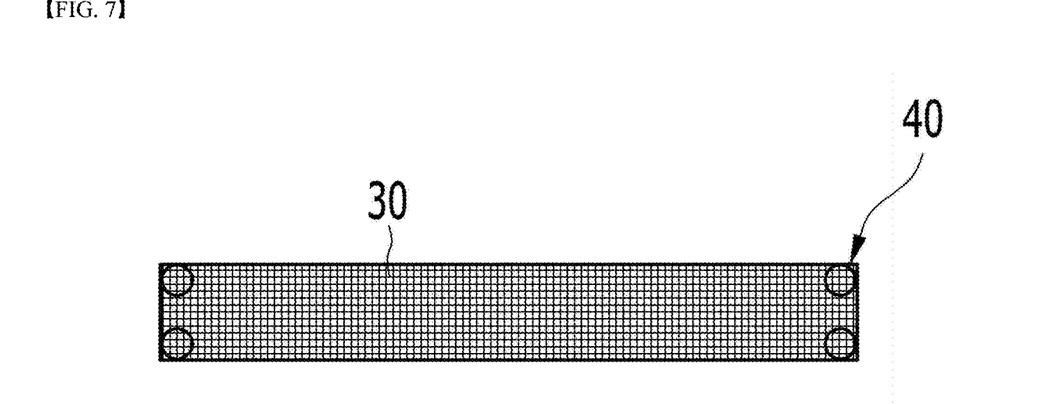
FIG. 7 is a schematic diagram showing a method of measuring a resistance of a welded portion by ultrasonic welding according to an embodiment of the present invention.

FIG. 7 is a schematic diagram showing a method of measuring a resistance to a welded portion according to an ultrasonic welding scheme. Referring to FIG. 7, a welded portion 30 formed by the ultrasonic welding scheme has the form of a line or a surface. As such, the contact position 40 of the resistance measuring probe for resistance measurement is positioned on the boundary line of the welded portion. The resistance of the entire welded portion can be measured by allowing the resistance measuring probe to contact the boundary line of the welded portion. There are 4 contact positions 40 of the resistance measuring probe. Herein, the current probe contacts two of the contact positions 40, and the voltage probe contacts the remaining two of the contact positions 40.

Figure 8:
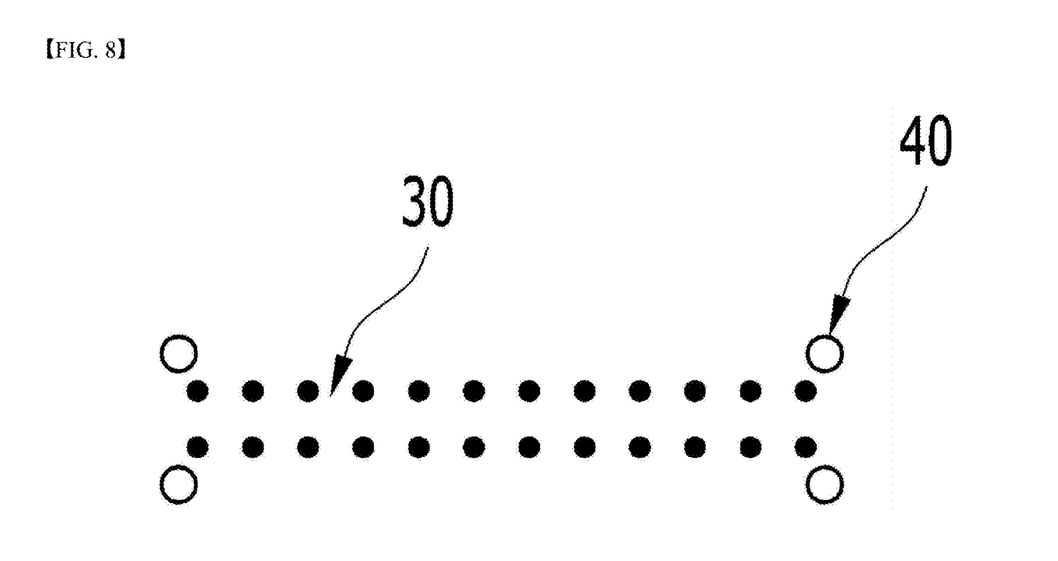
FIG. 8 is a schematic diagram showing a method of measuring a resistance of a welded portion by laser welding according to an embodiment of the present invention.

FIG. 8 is a schematic diagram showing a method of measuring a resistance to a welding portion according to a laser welding scheme. Referring to FIG. 8, the welded portion 30 formed by the laser welding scheme has a dotted shape. In order to measure the resistance of the entire welded portion, it is desirable to determine the contact position 40 of the resistance measuring probe on the outer peripheral surface with a virtual line obtained by connecting points at the outermost portions of the points as the boundary. There are 4 contact positions 40 of the resistance measuring probe. Herein, the current probe contacts two of the contact positions 40, and the voltage probe contacts the remaining two of the contact positions 40.

According to the welding inspection method of the present invention, resistances of a sample group are measured, a threshold resistance value is set from a normal distribution curve of the measured resistance values, and resistances are precisely measured by using a microresistance measuring instrument having a resolution of nanoohm to microohm levels when measuring resistances for the sample group and the welded portion to be inspected, thereby showing an excellent detection power for a weak welding defect.

The invention claimed is:

1. A method for inspecting a welding defect, comprising:
setting a threshold resistance including
measuring a first resistance of a first welded portion of a sample group using a microresistance measuring instrument having a resolution of nanoohm to microohm units, and
deriving a threshold resistance value which becomes an evaluation standard of a weak welding;
measuring a second resistance of a second welded portion to be inspected using the microresistance measuring instrument by contacting two resistance measuring probes with the second welded portion;
measuring a total resistance of the second welded portion by contacting one resistance measuring probe with one end of the second welded portion and contacting another resistance measuring probe with another end of the second welded portion; and
determining the second welded portion as a weak welding when the second resistance exceeds the threshold resistance value,
wherein the setting of the threshold resistance further comprises:
constructing data including measuring a microresistance of nanoohm and microohm units for a sample group and storing the measured microresistance; and
deriving the threshold resistance value by processing data accumulated in the constructing of data by a statistical scheme.

2. The method of claim 1, wherein the two resistance measuring probes each include a voltage probe and a current probe.

3. The method of claim 1, wherein the measuring of the second resistance includes measuring the second resistance by a 4-wire type measuring scheme.

4. The method of claim 1, wherein the measuring of the second resistance includes measuring the second resistance by a direct current scheme.

5. The method of claim 1, wherein a number of objects of the sample group is equal to or greater than 100,000.

6. The method of claim 1, wherein resistance values of the sample group form a normal distribution curve.

7. The method of claim 6, wherein the threshold resistance value is an average value+6δ.

8. The method of claim 1, wherein the second welded portion is an ultrasonic weld.

9. The method of claim 8, wherein the measuring of the total resistance includes contacting the resistance measuring probes with a boundary line of the second welded portion.

10. The method of claim 1, wherein the second welded portion is a laser weld.

11. The method of claim 10, wherein the measuring of the total resistance includes contacting the resistance measuring probes with an outer peripheral surface of the second welded portion.

12. The method of claim 1, wherein the second welded portion comprises a welded portion between an electrode lead and an electrode tab of a pouch-type secondary battery.

13. The method of claim 1, wherein the second welded portion comprises a welded portion between an electrode tab and an electrode tab of a pouch-type secondary battery.

* * * * *